United States Patent [19]
Hillsman

[11] Patent Number: 5,582,182
[45] Date of Patent: Dec. 10, 1996

[54] ABNORMAL DYSPNEA PERCEPTION DETECTION SYSTEM AND METHOD

[75] Inventor: Deane Hillsman, Sacramento, Calif.

[73] Assignee: Sierra Biotechnology Company, LC, McLean, Va.

[21] Appl. No.: 316,448

[22] Filed: Oct. 3, 1994

[51] Int. Cl.[6] .................................................. A61B 5/087
[52] U.S. Cl. ........................... 128/716; 128/720; 128/725
[58] Field of Search ..................................... 128/716, 720, 128/725

[56] References Cited

U.S. PATENT DOCUMENTS

| | | | |
|---|---|---|---|
| 3,621,833 | 11/1971 | Crane | 128/720 |
| 3,857,385 | 12/1974 | Hampl | 128/720 |
| 3,991,304 | 11/1976 | Hillsman . | |
| 4,984,158 | 1/1991 | Hillsman . | |

OTHER PUBLICATIONS (Poster Presentation and Abstract)–Lowered Chemosensitivity And Perception Of Dyspnea In Patients With Near–Fatal Asthma. Kikuchi, Y. et all. Respiratory and Critical Care Medicine; vol. 149, No. 4, Apr. 1994 (part 2), p. A929, Abstract No. A444.

(Scientific Papaer)–Chemosensitivity And Perception Of Dyspnea In Patients With A History Of Near–Fatal Asthma. Kikuchi, Yoshihiro, et all. The New England Journal of Medicine; vol. 330, No. 19, May 12, 1944, pp. 1329 to 1334.

*Primary Examiner*—Lee S. Cohen

[57] ABSTRACT

Apparatus and methods to test respiratory patients for altered dyspnea awareness. The device imposes a defined inspiratory resistive load under controlled breathing conditions and records the patient's subjective sensation of dyspnea over time by incrementally increasing the inspiratory resistive load. In a preferred embodiment, the patient breathes in a controlled manner with visual biofeedback prompting, having predetermined respiratory rate, inspiration to expiration time ratio and inspiration and expiration respiratory waveforms.

12 Claims, 5 Drawing Sheets

ABNORMAL DYSPNEA PERCEPTION DETECTION SYSTEM AND METHOD

BACKGROUND OF THE INVENTION

This invention relates to improved methods and apparatus to detect patients with an abnormally altered perception of dyspnea. Of particular concern are asthma patients at risk for fatal asthmatic attacks. An unexpected rising incidence of fatal asthmatic attacks in recent years has been of concern to the medical profession.

The sensitivity of the testing procedure is enhanced by the test being performed under controlled conditions by having the patient breathe in a precisely defined manner by visual biofeedback means, with the subject following a predetermined breathing pattern on a computer CRT or similar means. Hillsman incorporates by reference his U.S. Pat. No. 3,991,304 which describes a sophisticated method to prompt patients to desired breathing patterns by visual biofeedback means.

Prior art has indicated patients who have survived a near fatal asthma attack have decreased dyspnea awareness to increased inspiratory resistance (See: LOWERED CHEMOSENSITIVITY AND PERCEPTION OF DYSPNEA IN PATIENTS WITH NEAR—FATAL ASTHMA—Kikuchi, Y. et all, Respiratory and Critical Care Medicine, Supplement, Volume 149, Number 4, April 1994). The cited investigators demonstrated decreased dyspnea awareness in near fatal asthma patients by imposing graded inspiratory respiratory resistance from zero to minus 30 cm. water/liter/second gauge pressure. But no attempt was made by these investigators to further control the experimental conditions by defining the testing tidal volume to the patient's available lung volume as reflected in the patient's vital capacity, or the testing inspiratory resistance load to the patient's available maximum inspiratory pressure capability. Further, no attempt was made to otherwise precisely control the patient's breathing pattern or the precise timing of the breathing stages under the testing conditions, or to otherwise detect whether or not the subjects were performing as required under the testing conditions. Therefore, absent comprehensive controlled breathing conditions the testing achieved was relatively crude and therefore less sensitive to defining and detecting dyspnea awareness as measured by the commonly used Borg scale of dyspnea, and likewise there was no assurance as to patient performance and therefore data reliability.

In addition, there are many patients with Hyperventilation Syndrome, who perceive they have dyspnea when in fact their respiratory function is normal, and definition and quantifying this abnormality and normalization with treatment is of value in the patient therapeutic program.

Further, many patients with dyspnea related to Chronic Obstructive Pulmonary Disease (Emphysema and Chronic Bronchitis) and other respiratory conditions undergo comprehensive Pulmonary Rehabilitation, including various measures to improve dyspnea distress. These measures include various medications, breathing exercises and breathing retraining in proper breathing patterns, respiratory muscle reconditioning and strengthening by various means, and general body reconditioning and strengthening. Present methodology to quantify dyspnea and measure improvement with the various treatment modalities has generally been controversial and unsatisfactory. Therefore, there is a need to properly define and quantify the dyspnea abnormality and any normalization with the various treatments in the patient therapeutic program, both to guide therapy and to document improvement for administrative needs.

The instant invention to comprehensively define the testing conditions relative to the patient's vital capacity and/or maximum inspiratory pressure capability, and to further define the testing conditions by having the patient breathe in a precisely controlled manner using predefined breathing patterns by visual biofeedback means, and to precisely control the sequence and timing of the testing events. Therefore, by establishing the breathing testing conditions the sensitivity, accuracy and reproducibility of the diagnostic methodology will be enhanced. In addition, by placing definable plus and minus error limits above and below the desired breathing analogs, with suitable audio and/or visual alarms to indicate if the patient breathing performance is outside acceptable limits, the diagnostician may determine whether or not the subject is performing in an acceptable manner to the testing methodology as defined by the operator for the particular subject and thereby generating reliable testing data.

SUMMARY OF THE INVENTION

It is therefore one object of the present invention to enhance the sensitivity of testing for dyspnea awareness by the testing procedures being precisely controlled as to breathing patterns with defined elements of respiratory rate, inspiration to expiration time ratio, and inspiration and expiration breathing waveform analogs by visual biofeedback prompting means.

It is another object of the invention to enhance testing sensitivity in a first mode of operation by relating the testing tidal volume breath to a defined percentage of the patient's vital capacity capability, and to observe the patients dyspnea awareness under controlled respiratory stress conditions to detect abnormal response.

It is yet another object of the invention to enhance testing sensitivity in a first mode of operation by relating the testing inspiratory restive load to a defined percentage of the patient's maximum inspiratory pressure capability. A variable resistive load can be imposed by either a so-called non-linear adjustable "pinhole" orifice restrictive device or a so-called inspiratory "threshold" loading device, the non-linear resistive device being preferred in the present embodiment.

It is still another object of the invention to insure data integrity in all testing procedures by having the patient's breathing performance during testing take place between definable percentage plus and minus tidal volume error limits, and to indicate on the patient's breathing signal what zone of reliability they are operating within, and to indicate with alarm means when breathing performance is unsatisfactory.

It is a further object of the invention to have the patient indicate freely on a sliding electro-mechanical device their Borg Unit level of dyspnea awareness, on a scale of zero to ten (0 to 10), with automatic input of same to computer display and storage means.

It is an additional objective of the invention to permit testing other perceptual abnormality of patients for excessive dyspnea awareness, such as may occur in the Hyperventilation Syndrome.

It is a further additional objective of the invention to permit testing other perceptual abnormality of patients for excessive dyspnea awareness, such as may occur in Chronic Obstructive Pulmonary Disease, such as Emphysema and/or Chronic Bronchitis, and/or other respiratory conditions.

It is a final object of the invention to enhance testing sensitivity in a second mode of operation by controlling the testing breathing pattern by visual biofeedback means while introducing progressive inspiratory loads precisely and automatically at predetermined time intervals.

These objectives are achieved by a computer based controlling system that displays the desired patient breathing patterns and real time patient performance for patient biofeedback breathing control, and the patient indication of Borg defined units of dyspnea level. Inspiratory pressure is sensed, input to the computer and automatically adjusted to predetermined levels. Data integrity is assured by automated detection of the patient's breathing pattern exceeding plus or minus tidal volume percentage error limits, with appropriate indicating alarms.

In the first mode of operation the patient follows the prescribed breathing pattern and tidal volume based on a percentage of the patient's vital capacity at a constant inspiratory pressure predetermined as a percentage of the patient's maximal inspiratory pressure. The resultant data is plotted on a graph with the Borg Unit dyspnea level plotted on the vertical "y" ordinate axis versus Time on the horizontal "x" abscissa axis. Also numerically indicated at one minute intervals are the number of times the patient's breathing performance failed to remain within acceptable plus and minus defined parameter error limits.

In the second mode of operation the patient follows the prescribed breathing pattern and tidal volume based on a percentage of the patient's vital capacity at progressively increasing inspiratory resistive loads, starting a zero load and then automatically increasing by suitable increments, e.g. minus 5 cm. water pressure at suitable time intervals, e.g. every two minutes. The resultant data is plotted on a graph with the Borg Unit dyspnea level on the vertical "y" ordinate axis versus Time on the Horizontal "x" abscissa axis, and in addition the inspiratory pressures are plotted on the vertical "y" axis. Also numerically indicated at one minute intervals are the number of times the patient's breathing performance failed to remain within acceptable plus and minus defined parameter error limits.

These and other objects of the invention will be seen in the following description and in the drawing.

DESCRIPTION OF PREFERRED EMBODIMENTS

In the following description, metric units and standard respiratory terminology as defined by the American College of Chest Physicians are employed unless otherwise stated. Particular attention is directed toward the testing of human subjects for susceptibility to fatal asthmatic attacks by detecting a decreased awareness of dyspnea distress during the imposition of an inspiratory resistance load. This has been found to be a valid method to test asthmatic patients in this regard, but the known methods have employed relatively simple methodology that fails to standardize the testing conditions adequately. The method and apparatus may alternatively be used to test subjects for excessive dyspnea awareness as may be present in the abnormal perception-related condition of Hyperventilation Syndrome, or to define and quantify the dyspnea of patients with Chronic Obstructive Pulmonary Disease and/or other respiratory conditions.

The underlying object of this invention is to define testing conditions for all appropriate pulmonary function testing procedures in a more precise manner by visual biofeedback means, where the subject is encouraged to follow precisely defined inspiration and expiration visual analogs and thereby make the sensitivity, accuracy and reproducibility of the tested parameter optimally standardized. This is based on the general observation that the sophistication of modern pulmonary function testing equipment is usually more accurate than the methodology and the physiologic parameter being tested, due to the natural variability of native patient breathing patterns, and the alteration of these breathing patterns under testing conditions. Therefore, to improve the accuracy of the relevant pulmonary function test, the variable patient breathing patterns must be standardized and quality controlled in order the measuring equipment and the measuring methodology produce more valid data on the tested patient functional parameter.

The underlying concept of the instant invention relates to precise breathing control using defined visual inspiration and expiration analogs for the subject to follow, with the subject's respiratory Tidal Volume defined as a predetermined percentage of their Vital Capacity, and the Inspiratory Resistance load a predetermined percentage of the subject's Maximum Inspiratory Pressure; or alternatively the Inspiratory Resistance being predetermined time incremental steps of predetermined resistance loads, and to automate the procedure.

In the preferred embodiment the patient sees a visual analog of inspiration and expiration on a computer CRT or TV display, and with a simultaneous display also visualizes their real time breathing performance analog, with the Tidal Volume breath indicated on the vertical "y" ordinate axis plotted against Time on the horizontal "x" abscissa axis. The patient is instructed to match their real time breathing performance to the desired performance analog as indicated by flashing cursor means in the appropriate time domain using so-called visual biofeedback means; thereby conforming the patient's breathing to a defined standard breathing pattern. The Tidal Volume breath is determined as a defined standard percentage, generally between 25% and 50% of an independently measured Vital Capacity breath. The Inspiratory Resistive negative pressure load is determined as a defined standard percentage, generally between 25% and 75% of an independently measured Maximum Inspiratory Pressure. The Respiratory Rate is defined generally between 5 and 15 breaths per minute. The Inspiration to Expiration Time Ratio is defined generally between 1:1 and 1:3. The Inspiratory Pause Time is defined as a percentage of the Inspiratory Time generally between zero and 10%, and the Expiratory Pause Time is defined as a percentage of the Expiratory Time generally between zero and 25%. The Inspiration and Expiration waveforms are defined as linear or various curvilinear forms. Thus all the components of the breathing cycle may be defined precisely and displayed as a visual analog of breath volume plotted against time, and with the patient following the breathing analog at the flashing cursor the method therefore becomes an instantaneous breath flow controller as dictated by the fundamental equation Volume=Flow X Time. In another mode of operation multiple plus and minus analog error limits as a percentage of the Tidal Volume may be defined and optionally displayed, to detect patient performance falling outside defined limits, with suitable auditory and/or visual alarms to indicate deficient performance. Optionally the error limit analogs may be hidden from display, with the displayed patient breathing signal changing shape and/or color depending on which error limit the patient's breathing performance is operative.

In the preferred embodiment the Inspiratory Resistive Load remains constant, with the patient attempting to maintain the desired breathing pattern until unable to maintain said standardized breathing pattern due to fatigue or excessive respiratory distress. At one minute intervals the patient is prompted to indicate their perceived dyspnea level in standard Borg numeric units on a scale of zero to ten (0 to 10), zero indicative of no perceived dyspnea and ten being indicative of maximal perceived dyspnea, by sliding a pointer along a linear potentiometer or similar device for data input. In an alternate mode of operation the Inspiratory Resistive Load is progressively incremented in predetermined negative pressure loads expressed as cm. water, for example zero, –2, –5, –10, –15, –20, –25, –30, etc. cm. water at time intervals between 1 and 3 minutes. Inspiratory pressures, the integrated respiratory flow/Tidal Volume, and Borg Dyspnea Units are stored in computer memory, and are reported in graphic form, the Borg Dyspnea Units and Inspiratory Pressure plotted on the vertical "y" axis coordinate against Time on the horizontal "x" axis coordinate. Optionally the Tidal Volumes may be similarly displayed on the vertical "y" axis coordinate. In this manner the patient's level of dyspnea may be plotted against a standardized breathing pattern and inspiratory load stress, the normal subject indicating progressive dyspnea, and those subjects susceptible to asthmatic hazard and potential fatality indicating a minimal dyspnea response to progressive inspiratory muscle resistive stress, and with Hyperventilation Syndrome patients and those subjects with Chronic Obstructive Pulmonary Diseases and/or other pulmonary pathological conditions indicating excessive dyspnea at inappropriately low inspiratory work loads.

In the preferred embodiment the testing process is automated in the appropriate time domain, by feedback computer control of inspiratory pressure adjusting a variable inspiratory resistance device by means of a computer feedback controlled stepping motor. Inspiration Pressures, Tidal Volume, Borg Unit data and the minute by minute frequency of patient failure to achieve acceptable breathing performance is stored in computer memory for display and analysis. In an alternate mode of operation the operator may manually adjust the inspiratory pressure with reference to a separate mechanical pressure gauge.

This invention is general as to means and method to control breathing during breathing testing, and specific as to means and method to control breathing in a standardized manner while testing for dyspnea awareness with increasing inspiratory resistance loading and stress of inspiratory muscles, to thereby reveal patients with inappropriate and reduced breathing awareness that might subject them to asthma hazard and potential fatality, though the inventive concept would not be limited to specific testing for dyspnea awareness with inspiratory loading. This invention could also be used specifically to test patients for excessive dyspnea awareness as may be present in the condition of Hyperventilation Syndrome and a variety of pulmonary pathologic conditions, including Chronic Obstructive Pulmonary Diseases and/or pulmonary Restrictive Diseases.

Figure 1:
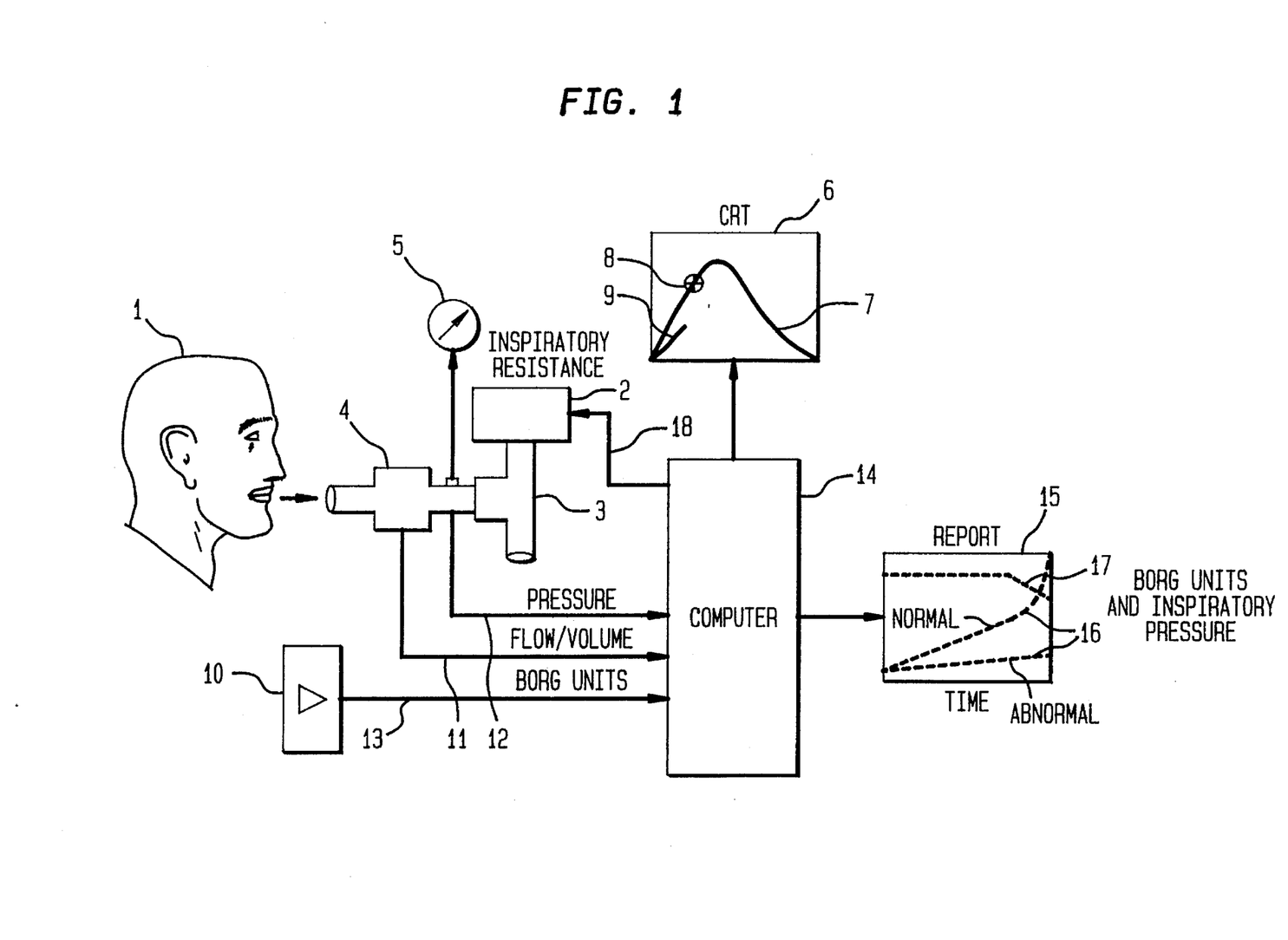
FIG. 1 is a simple schematic diagram of the overall system.

Referring to the simplified schematic diagram in FIG. 1 the Patient (1) inspires air through Inspiratory Resistance Device (2) via Directional Respiratory Valve (3). Inspiratory and expiratory air is sensed by Flowmeter (4) and Mechanical Pressure Meter (5). The Patient (1) observes CRT (6) to visualize Prescribed Breathing Pattern (7) and by visual biofeedback means following Prompting Cursor (8) attempts to place their real time Breathing Signal (9) on the Prescribed Breathing Patten (7). At one minute intervals the patient is prompted to indicate their perceived level of dyspnea on an electro-mechanical Linear Potentiometer (10) calibrated in zero to ten Borg Dyspnea Units. Suitable differential pressure transducer and integrator means in conjunction with Flowmeter (4) senses respiratory flow which is integrated into Tidal Volume Signal (11), and suitable pressure transducer means provides Respiratory Pressure Signal (12) and Linear Potentiometer (10) provides Borg Units Signal (13), all of which are input to Computer (14) data storage and control means, to be output to Graphic Report (15) of Borg Dyspnea Display (16) and Inspiratory Pressure Display (17) plotted against Time. Computer (14) provides Inspiratory Resistance Feedback Control Signal (18) to Inspiratory Resistive Device (2).

Figure 2:
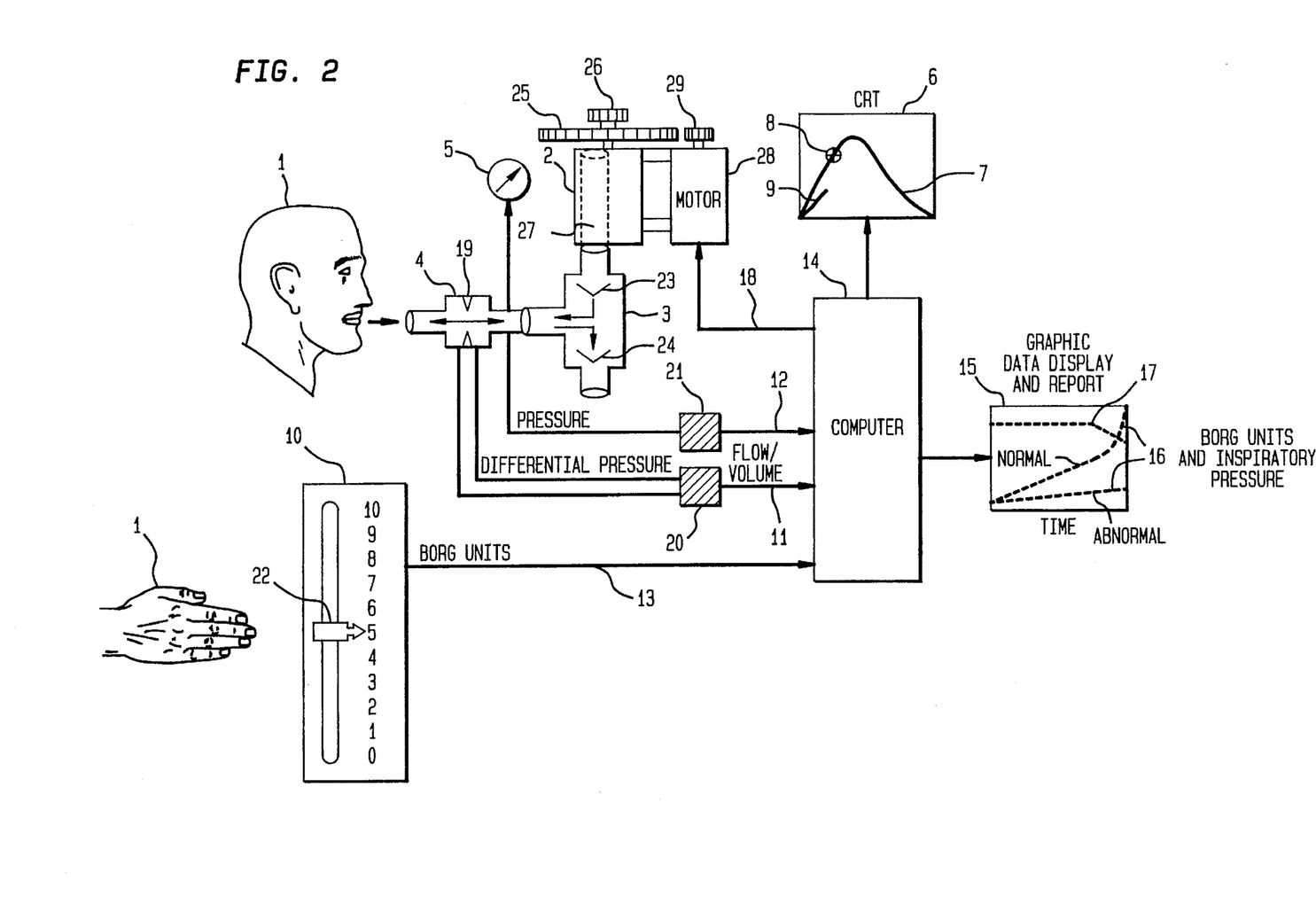
FIG. 2 is a schematic diagram of the system and patient interactive devices.

The schematic diagram in FIG. 2 is a more detailed overall description of the system design and the patient interactive devices. Patient (1) breaths through Flowmeter (4) which provides a differential pressure due to Flowmeter Restrictions (19). The flow generated differential pressure is sensed on each side of Flowmeter Restrictions (19) and detected by Differential Pressure Transducer (20) with subsequent signal conditioning and analog to digital conversion by suitable hardware and/or software means for input of Tidal Volume Signal (11) to Computer (14). Optionally the differential pressure detection, signal conditioning and analog to digital conversion may be within Computer (14) or by external devices. Respiratory pressure is sensed by Mechanical Pressure Meter (5) and Pressure Transducer (21) with subsequent signal conditioning and analog to digital conversion by suitable hardware and/or software means for input of Respiratory Pressure Signal (12) to Computer (14). Optionally the pressure detection, signal conditioning and analog to digital conversion may be within Computer (14) or by external devices. Within Computer (14) all inspiratory and expiratory pressures at suitable sampling rates, for example 100 Hz., are stored breath by breath in suitable computer memory array means, and pattern recognition algorithms detect and similarly store Peak Inspiratory Pressure and Average Inspiratory Pressure. Patient (1) in response to perceived dyspnea level manipulates sliding scale Pointer (22) on Linear Potentiometer (10) to provide Borg Units Signal (13) to Computer (14). Respiratory flow is directed by Directional Respiratory Valve (3) by Inspiration Valve (23) and Expiration Valve (24) which vents the patient's unobstructed exhaled breath to room air. Patient (1) inspires through Directional Respiratory Valve (3) which is attached to Inspiratory Resistive Device (2). Variable inspiratory respiratory resistance is provided by Respiratory Resistance Plate (25) which exposes a variable sized orifice to Inspiration Chamber (27) by the operator rotating Respiratory Resistance Plate (25) manually by Handle (26) while observing Mechanical Pressure Meter (5). In the preferred embodiment Respiratory Pressure Signal (12) is compared to a predetermined desired inspiratory pressure and Computer (14) generates an appropriate Inspiratory Resistance Feedback Control Signal (18) to Stepping Motor (28) and Reduction Gear (29) to turn Respiratory Resistance Plate (25) to achieve the desired inspiratory pressure. Patient (1) observes CRT (6) to visualize Prescribed Breathing Pattern (7) and by visual biofeedback means following Prompting Cursor (8) attempts to place their real time Breathing Signal (9) on the Prescribed Breathing Patten (7). At one minute intervals the patient is prompted to indicate their perceived level of dyspnea by Pointer (22) on electro-mechanical Linear Potentiometer (10) calibrated in zero to ten Borg Dyspnea Units. At the conclusion of the test, or optionally dynamically on a second CRT, data display and Graphics Report (15) are generated for direct viewing or hard copy report. The Borg Dyspnea Display (16) units and Peak Inspiratory Pressure Display (17) units in cm. water, or optionally the Average Inspiratory Pressure, is plotted on the vertical "y" axis ordinate versus Time on the horizontal "x" axis abscissa.

Figure 3A:
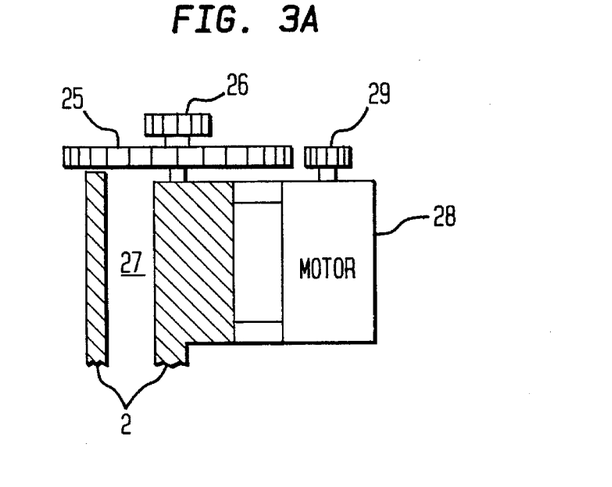
FIG. 3a is a side view of the Airway Resistor/Stepping Motor Assembly.
Figure 3B:
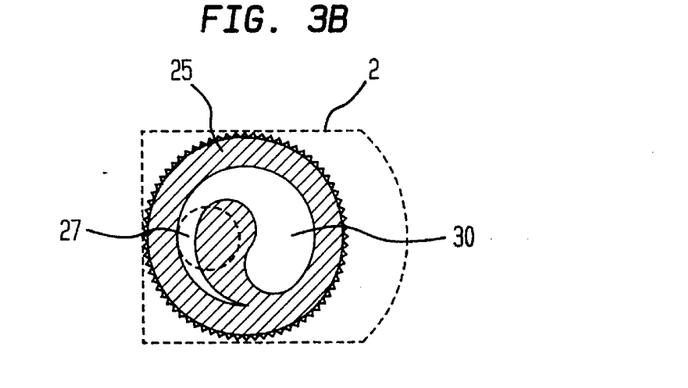
FIG. 3b is a top view of the Airway Resistive Device.
Figure 3C:
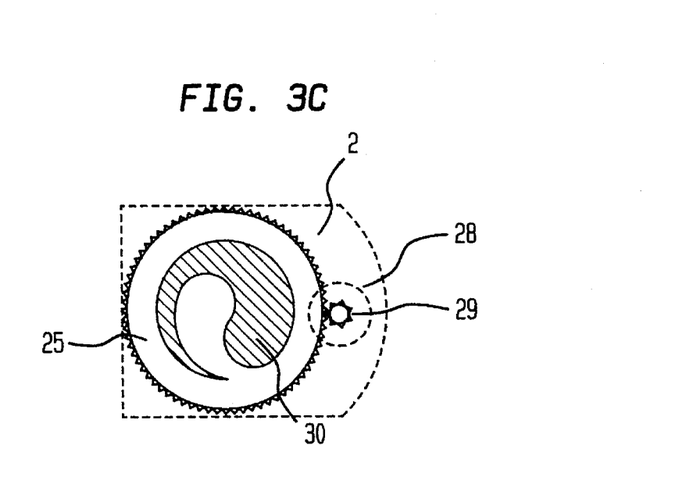
FIG. 3c is a side view of the Airway Resistor/Stepping Motor Assembly.
Figure 4A:
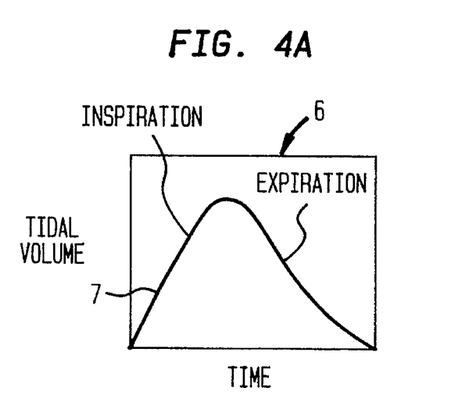
FIG. 4a is a display of the patient prompting program breathing analogs.
Figure 4B:
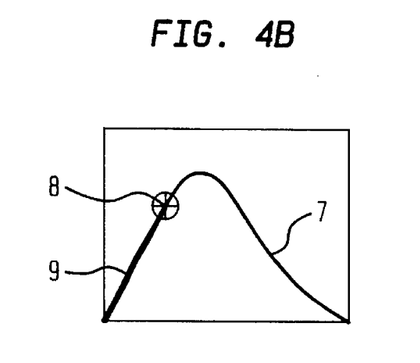
FIG. 4b is a display of proper patient breathing performance matching the prompting analog display.
Figure 4C:
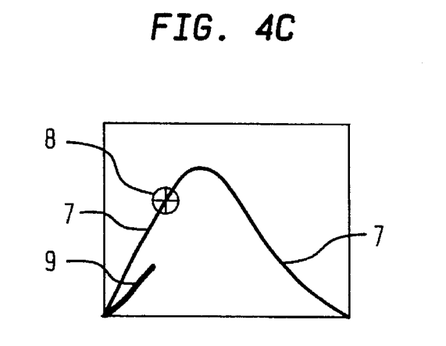
FIG. 4c is a display of inadequate patient breathing performance, not achieving the cursor prompted analog display.
Figure 4D:
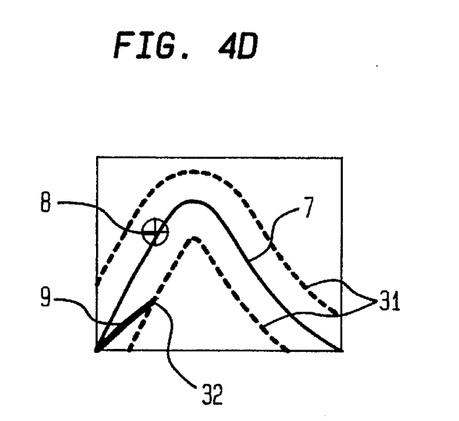
FIG. 4d is a display of plus and minus Phantom Line error limits, and the detection of inadequate patient performance.
Figure 4E:
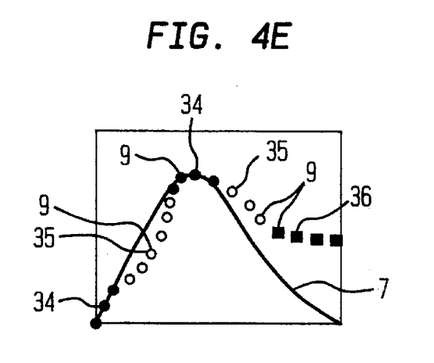
FIG. 4e is a display of the prompting breathing analog and the patient real time breathing performance, with changing symbols and/or color depending on which error limit the patient's breathing is operative.
Figure 4F:
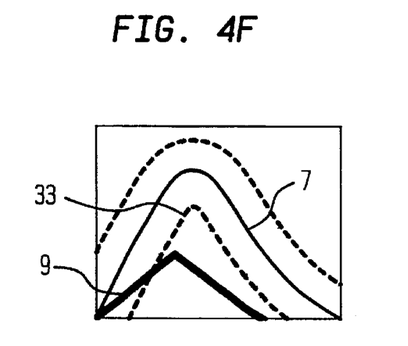
FIG. 4f is display of an exhausted patient unable to maintain performance requirements and therefore termination of the test.

The schematic diagram in FIG. 3 is a more detailed overall description of the Inspiratory Resistive Device (2). FIG. 3a.) is a side view of Inspiratory Resistive Device (2) and Stepping Motor (28) with Reduction Gear (29) meshing with Respiratory Resistance Plate (25). Respiratory Resistance Plate (25) rotates about a central mount on Respiratory Resistance Device (2) and has a Handle (26) to assist manual rotation to permit a variable sized orifice to be exposed to Inspiration Chamber (27). FIG. 3b.) is a top view of Inspiratory Resistive Device (2) and Inspiration Chamber (27) with centrally mounted Respiratory Resistance Plate (25) containing Variable Orifice (30). As Respiratory Resistance Plate (25) is rotated the opening of Inspiration Chamber (27) will be constricted to a greater or lesser degree, thereby producing a greater or lesser degree of inspiratory resistance. FIG. 3c.) is a top view of Inspiratory Resistive Device (2) and Stepping Motor (28) with Reduction Gear (29) meshing with Respiratory Resistance Plate (25), thereby permitting motor adjustment of Variable Orifice (30) to automatically adjust airway resistance by computer controlled feedback means.

The schematic diagrams in FIG. 4 describes various visual biofeedback images seen on CRT (6). FIG. 4a.) shows Prescribed Breathing Pattern (7) displayed where Tidal Volume is depicted on the vertical "y" ordinate axis plotted against Time on the horizontal "x" abscissa axis, indicating Inspiration in an upward direction and Expiration in a downward direction. FIG. 4b.) indicates proper patient biofeedback breathing performance with the patient Breathing Signal (9) superimposed on Prescribed Breathing Pattern (7) at Prompting Cursor (8). FIG. 4c.) indicates inadequate patient biofeedback breathing performance with the patient Breathing Signal (9) falling below Prescribed Breathing Pattern (7) and Prompting Cursor (8). FIG. 4d.) is identical to FIG. 4c.) and in addition shows plus and minus Phantom Line Error Limits (31) above and below Prescribed Breathing Pattern (7) with a Negative Error Limit Detection (32) to trigger appropriate audio and/or visual alarms. Not shown are multiple Phantom Line error detection limits, for example error limits of plus and minus 10% of Tidal Volume, plus and minus 20%, plus and minus 30%, etc. FIG. 4e.) is a display of patient performance error detection without the display of the Phantom Lines, wherein only Prescribed Breathing Pattern (7) and patient Breathing Signal (9) appear. In this option the patient Breathing Signal (9) changes to different graphic characters and/or colors, depending on which zone of error detection the patient performance is operative. For example, perfect matching of the patient's breathing performance with Prescribed Breathing Program (7) might be indicated by a Small Closed Circle (34), acceptable breathing performance within plus and minus 10% indicated by a Small Open Circle (35), and unacceptable patient performance in excess of plus and minus 25% indicated by Small Closed Squares (36). FIG.4f.) is a display of patient exhaustion wherein the Patient Breathing Signal (9) is unable to follow Prescribed Breathing Program (7) and is unable to achieve a minimal Tidal Volume as depicted by Negative Error Limit (33) and thus indicating the need to terminate the testing procedure.

Figure 5A:
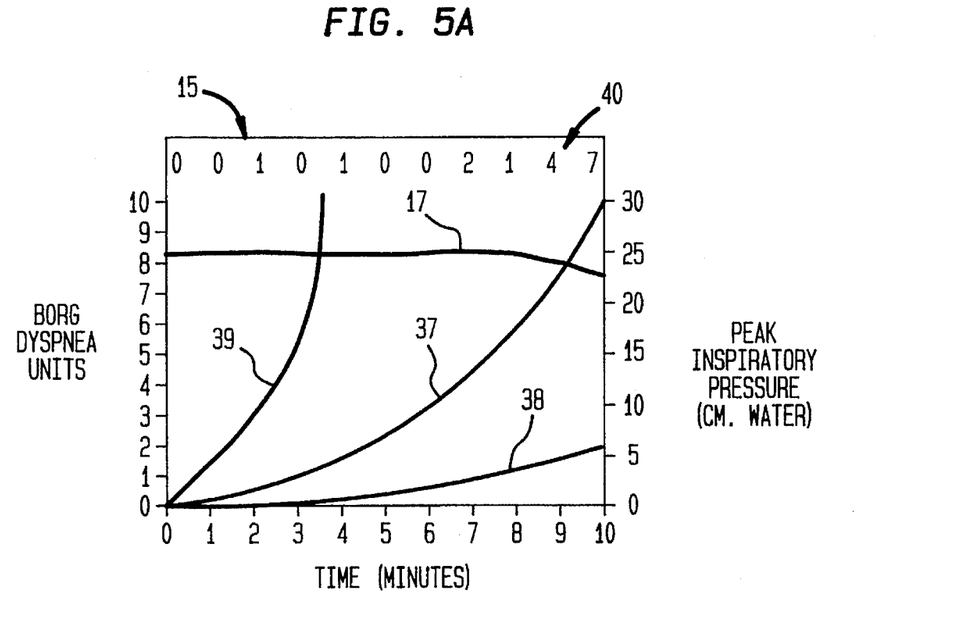
FIG. 5a is a display of Constant Inspiratory Resistance plotting the Borg Dyspnea Scale and Inspiratory Pressure against time.
Figure 5B:
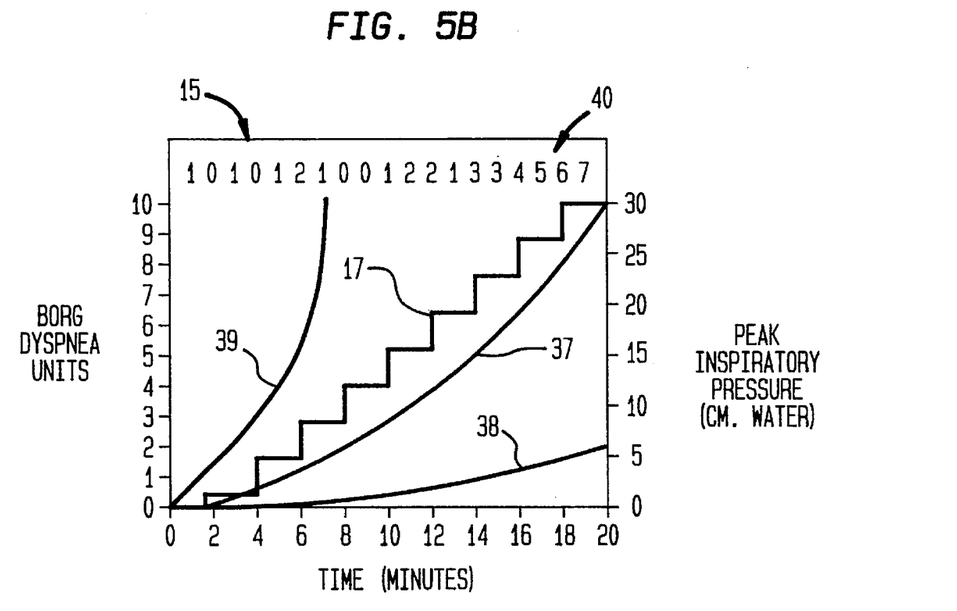
FIG. 5b is a display of Incremental Inspiratory Resistance plotting the Borg Dyspnea Scale and Inspiratory Pressure against time.

The schematic diagrams in FIG. 5 describes various CRT graphic displays and/or hard copy printed reports of the derived data. FIG. 5a.) is the preferred embodiment wherein the testing procedure has been with constant prescribed inspiratory resistance load, as determined by a predetermined percentage of the Maximum Inspiratory Capacity. Graphics Report (15) plots Borg Dyspnea Units and Peak Inspiratory Pressure on the vertical "y" ordinate axis, against Time on the horizontal "x" abscissa axis. Optionally Average Inspiratory Pressure may be substituted for Peak Inspiratory Pressure. Inspiratory Pressure Display (17) in this mode of operation is a generally a straight line throughout most of the testing procedure, reflecting the ability of the patient to inspire the prescribed Tidal Volume breath within the defined parameters of Prescribed Breathing Pattern (7). Near the end of the testing procedure the inspiratory pressure tends to diminish, reflecting patient exhaustion and the inability therefore to inspire the full prescribed Tidal Volume breath, though in some cases the patient may maintain their ability to breathe as prescribed despite fatigue and severe dyspnea. Numeric Parameter Limit Failure (40) is accumulated and indicated at one minute intervals, and as indicated with increased failure of breathing control as the patient becomes exhausted. A Normal Borg Response (37) to progressive fatigue is indicated. Also shown is abnormal Diminished Borg Response (38) thereby indicating the patient to be susceptible of developing severe or potentially fatal asthmatic exacerbations as such patients are relatively unaware of the severity of their condition and therefore may not promptly seek appropriate urgent medical attention. Also shown is Excessive Borg Response (39) as may be seen in subjects susceptible to the condition of Hyperventilation Syndrome, or subjects with pulmonary pathologic conditions such as Chronic Obstructive Pulmonary Disease. FIG. 5b.) is an alternate testing method wherein the inspiratory resistive load is applied in incremental steps at prescribed times, e.g. two minute intervals, and with prescribed resistive loads at each incremental step, e.g. zero, −2, −5, −10, −15, −20, −25, −30, etc. cm. of water pressure, with the patient breathing in a prescribed manner according to Prescribed Breathing Pattern (7). Displayed are examples of Normal Borg Response (37), Diminished Borg Response (38) and Excessive Borg Response (39) and numeric Parameter Limit Failure (40) events.

What is claimed is:

1. A method for monitoring an asthma patient to determine decreased ability to perceive severe respiratory distress, comprising:

measuring the patient's respiration vital capacity for establishing controlled patient tidal volume;

measuring the patient's respiration maximal inspiratory pressure capacity for establishing controlled patient inspiratory resistive load;

establishing visual patient inspiration and expiration breathing pattern comprising determined tidal volume, respiratory rate, inspiration to expiration time ratio, and inspiration and expiration waveforms;

applying external inspiratory flow resistance determined from maximal inspiratory pressure while maintaining substantially controlled patient respiration; and evaluating patient dyspnea subjective perception response to said inspiratory flow resistance under conditions of controlled breathing to determine patient dyspnea perception to severe or potentially fatal asthma attack due to the patient's inability to perceive asthma severity.

2. The method of claim 1 wherein said measuring steps include the steps of measuring patient's tidal volume, inspiration rate and expiration rate at ambient pressure in the absence of substantial external inspiratory resistance; and wherein stored normal respiration is retrievable for display and comparison.

3. A method for monitoring an asthma patient to determine susceptibility to severe respiratory disfunction, comprising:

measuring respiration and establishing patient respiration data, including normal inspiration and expiration patterns and vital capacity;

storing the measured respiration data for retrieval and display;

displaying a prescribed inspiration- expiration curve having a tidal volume substantially less than vital capacity for visual feedback and comparison of patient performance under dynamic testing conditions;

applying variable external inspiratory flow resistance while maintaining patient respiration performance complying with the prescribed curve; and evaluating patient response to said inspiratory flow resistance to determine the patient's relative ability to perceive respiratory distress.

4. The method of claim 3 wherein said measuring step includes the step of measuring tidal volume, inspiration rate and expiration rate at ambient pressure in the absence of substantial external inspiratory resistance; and setting inspiration rate of the prescribed curve under dynamic testing conditions at about 50% of measured normal inspiratory maximum.

5. The method of claim 3 including the step of increasing the external inspiratory flow resistance incrementally to about 60 cm water differential pressure.

6. A diagnostic method for determining a human patient's predisposition to abnormal dyspnea perception, comprising:

establishing the patient's respiratory performance parameters of tidal volume and air flow during at least one respiratory cycle;

imposing a physical resistance to normal respiration, while requiring the patient to perform respiratory functions to achieve a predetermined parameter; and evaluating the patient's subjective response to respiratory stress in achieving said predetermined parameter.

7. The diagnostic method of claim 6 wherein the predetermined parameter is a fraction of maximum tidal volume; and wherein the physical resistance comprises inspiratory air flow resistance.

8. The diagnostic method of claim 7 including the step of increasing the inspiratory resistance incrementally in a series of respiratory cycles, while maintaining a prescribed respiratory flow pattern; and evaluating respiratory stress by subjective patient response.

9. The diagnostic method of claim 8 wherein the patient achieves at least 50% of the patient's predetermined maximum tidal volume, as measured prior to imposing external air flow resistance at ambient pressure; and including the step of varying the inspiratory air flow resistance over a differential pressure range from ambient to at least 30 cm water pressure.

10. A diagnostic method for determining a human patient's perception of dyspnea, comprising:

establishing patient respiratory performance parameters of tidal volume and air flow during at least one respiratory cycle;

imposing a physical resistance to normal respiration, while requiring the patient to perform respiratory functions to achieve a predetermined parameter; wherein the predetermined parameter is a fraction of maximum tidal volume; and wherein the physical resistance comprises increasing incrementally inspiratory air flow resistance in a series of respiratory cycles, while maintaining a prescribed respiratory flow pattern; and evaluating respiratory stress by subjective patient response to perceived dyspnea, wherein the respiratory stress is expressed as inspiratory muscle discomfort and/or fatigue.

11. The diagnostic method of claim 10 wherein the patient achieves at least 50% of the patient's predetermined maximum tidal volume, as measured prior to imposing external air flow resistance at ambient pressure; and including the step of varying the inspiratory air flow resistance over a differential pressure range from ambient to at least 30 cm water pressure.

12. Evaluation apparatus for monitoring asthma patients to determine subjective perception of respiratory distress, comprising:

a plumonary function device for measuring patient respiration vital capacity to establish controlled patient tidal volume;

a respiratory flow measurement and display device for measuring patient inspiration and expiration performance and displaying said performance concurrently with prescribed tidal volume, respiratory rate, inspiration: expiration time ratio, and inspiration and expiration waveforms, said measurement and display device employing a prescribed inspiration- expiration curve having a tidal volume substantially less than vital capacity for visual feedback and comparison of patient performance under dynamic testing conditions;

means for setting variable external inspiratory flow resistance determined from maximal inspiratory pressure under controlled patient respiration conditions and incrementally variable over a differential pressure range from 0 to at least 30 cm water pressure; and a comparison system for comparing patient dyspnea perception response to normal response to the inspiratory flow resistance under conditions of controlled breathing to determine patient dyspnea perception to severe asthma distress.

* * * * *